United States Patent [19]
Cohn

[11] 4,178,926
[45] Dec. 18, 1979

[54] PEDIATRIC RESTRAINT DEVICE

[76] Inventor: Arnold K. Cohn, 2086 Drury La., Northfield, Ill. 60093

[21] Appl. No.: 901,289

[22] Filed: May 1, 1978

[51] Int. Cl.² ............................................. A61F 13/00
[52] U.S. Cl. .................................................. 128/133
[58] Field of Search .............................. 128/132–135, 128/139; 5/100, 92, 329, 330

[56] References Cited

U.S. PATENT DOCUMENTS

| 2,044,390 | 6/1936 | Kiehs | 128/134 |
| 2,556,913 | 6/1951 | Gilbert | 5/330 |
| 3,482,566 | 12/1969 | Watkins | 128/133 |
| 4,017,920 | 4/1977 | Sieg | 5/92 |

FOREIGN PATENT DOCUMENTS

| 1012022 | 6/1977 | Canada | 128/139 |
| 160570 | 5/1933 | Switzerland | 128/135 |
| 7033 | of 1905 | United Kingdom | 128/135 |

Primary Examiner—Lawrence W. Trapp
Attorney, Agent, or Firm—Dressler, Goldsmith, Clement, Gordon & Shore, Ltd.

[57] ABSTRACT

A restraint device is positioned in a generally upright manner transversely to a child's waist to prevent a child's hands from reaching the lower half of the body which may have casts thereon or be in traction. The restraint device is a generally flat plate having a contoured bottom wall which overlies the child's waist, and is secured to the side rails of a bed by straps.

6 Claims, 2 Drawing Figures

PEDIATRIC RESTRAINT DEVICE

BACKGROUND OF THE INVENTION

This invention pertains to restraint devices and, more particularly, to a pediatric restraint device for preventing a child's hands from reaching his legs.

Children with broken bones in their thighs or lower extremities must frequently lie with casts or in traction for prolonged periods. A problem which results with children is that they use their hands to pick at the casts or traction. The children are sometimes able to pull the traction devices off their legs or remove portions of a cast; these are highly undesirable results which can have deleterious consequences to the recovery of the child.

In an attempt to overcome this problem, nurses have sometimes found it necessary to tie children's hands to the bed rails to prevent them from reaching the casts or traction devices. One of the disadvantages of such a procedure is the physical discomfort which it causes.

SUMMARY OF THE INVENTION

The present invention overcomes the foregoing problems by providing a restraint device which prevents a person's hands from contacting that person's legs while lying in a bed having side rails, while leaving that person's hands completely free and unrestrained. The device is typically used with children.

This is accomplished by providing a generally flat plate which is positioned in a generally upright manner transversely to the person along the person's waist. The plate has a bottom wall which is contoured to define a base portion at opposite ends which is positioned on the bed on opposite sides of the person's waist, and a central portion which overlies the person's waist.

The plate is releasably secured to the bed, as by a plurality of straps which each have one end secured to a marginal side portion of the plate, and a free end for securement to the side rails of the bed.

To soften any contact between the person's waist and the device, padding may be secured to the contoured portion of the bottom wall of the plate.

The plate has a length about equal to the width of the bed, and a height about equal to the height of the side rails of the bed. The plate can be a wooden board or can be formed of any suitable plastic or metal.

DETAILED DESCRIPTION OF THE PREFERRED EMBODIMENT

Figure 1:
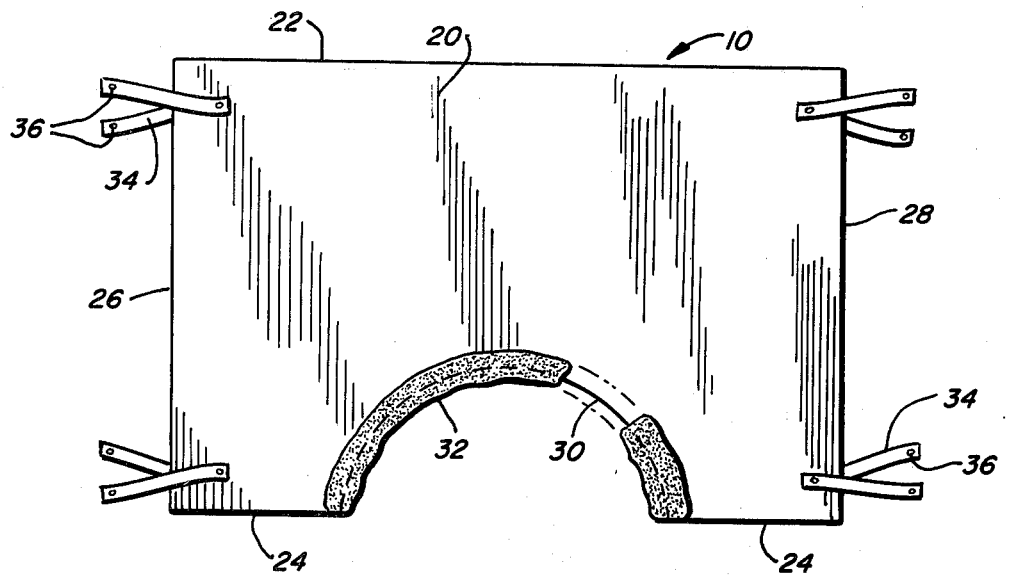
FIG. 1 is a front elevational view of the restraint device of the present invention, partially cut away to show interior construction.
Figure 2:
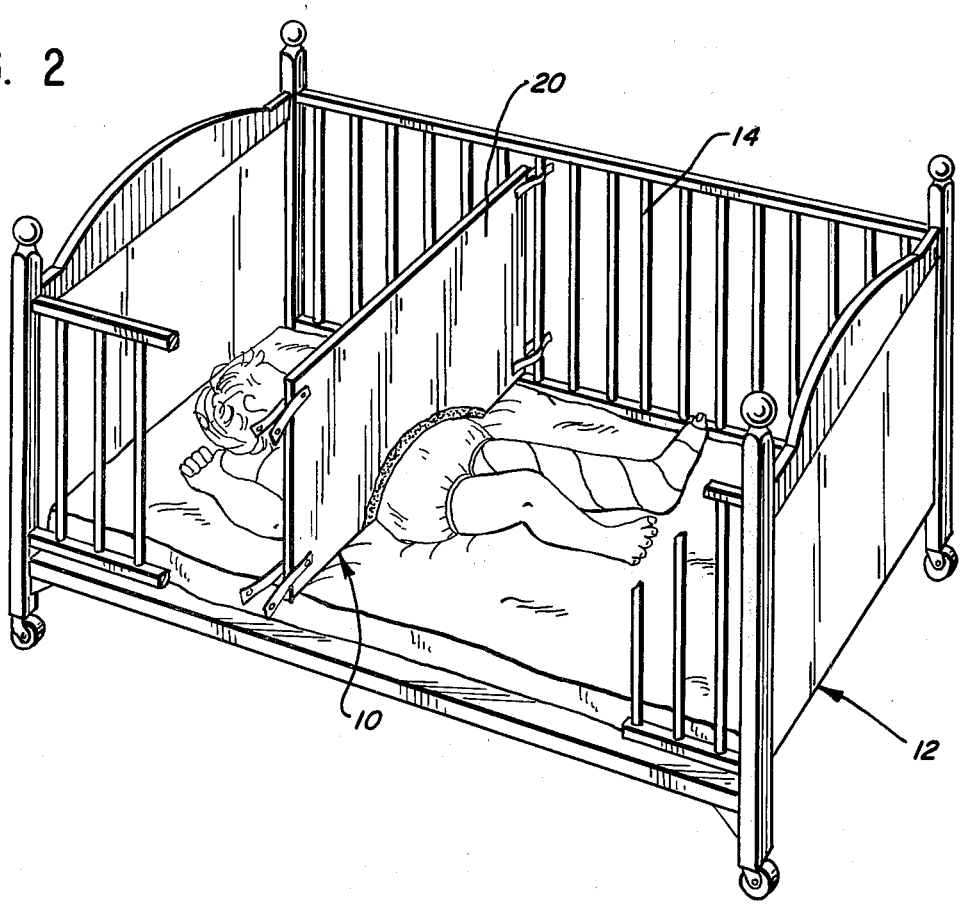
FIG. 2 is a perspective view of the restraint device of FIG. 1 in use in a bed having side rails, with the bed partially cut away.

Referring to FIGS. 1 and 2, the restraint device 10 of the present invention is adapted for use with a bed 12 having side rails 14. The bed may be a hospital bed or a crib.

The restraint device is a generally flat board or plate 20 which can be formed of wood or other suitable materials such as a plastic or metal. As shown in FIG. 2, the plate 20 is adapted for positioning in the bed 12 and has a length about equal to the width of the bed, and a height about equal to the height of the side rails 14. The plate 20 is generally rectangular and has a top wall 22 and a bottom wall 24 along the length of the plate, and a pair of side walls 26 and 28 extending for the height of the plate. The bottom wall 24 is contoured to conform to the waist of a person, and accordingly has a central cut-out portion 30 which defines a generally semi-circular opening between the plate and the bed for receiving a person's waist. The portion of the bottom wall 24 on both sides of the contoured central portion defines a base which is positioned on the top surface of the bed on opposite sides of the person's waist.

The restraint device in accordance with the present invention is intended for use with persons having broken bones in their thighs or lower extremities and is intended to prevent the person from reaching a cast or traction device with that person's hands. The restraint device is most typically used for children.

Although a person having a cast and/or traction device is largely immobilized, that person can nevertheless shift position which can change the position of the bones which could be harmful to the person's recovery. The restraint device 10 overcomes this problem by preventing the person from moving his waist laterally or upwardly. Thus, the lower half of the person's body is kept from making significant changes in position which would change the position of the bones below the waist.

Another problem which is overcome by the present invention is that persons use their hands to remove portions of the cast or pull the traction devices off their legs. The restraint device 10 eliminates this problem by providing an obstacle which prevents the person's hands on one side of the restraint device from reaching the person's cast or traction device on the other side of the restraint device.

It is a particular feature of the present invention that the foregoing problems associated with casts or traction devices on the thighs or lower extremities are overcome while allowing the person's hands and arms virtually complete freedom of movement.

As can be seen from the foregoing, it is unnecessary to have a snug fit between the person's waist and the contoured central portion of the bottom wall. It is sufficient that any gap between the person's waist and the contoured central portion is too small to permit the person's hands and arms from extending through the gap.

Since small movements may bring the waist area of the person into contact with the contoured central portion of the bottom wall of the plate, padding 32 is provided to cushion the contact. The padding may be foam rubber or other suitable materials, and is secured to the contoured central portion 30 of the bottom wall.

Straps 34 are provided for securing the plate 20 to the side rails 14 of the bed 12. Each strap 34 has one end permanently secured to a marginal side portion of the plate, and an opposite free end for securement to the side rails of the bed. For example, conventional snaps 36 can be attached to the straps, whereby each strap is wrapped around one of the vertical bars of the side rail, and the strap is then snapped together to secure the plate to the side rail. The straps are preferably formed of leather or stretchable materials. Along each marginal side portion of the plate, there are two sets of straps— one which is proximate the top wall 22 of the plate and the other which is proximate the bottom wall 24 of the plate. When all of the straps 34 are fastened, the plate is tautly secured to the side rails of the bed.

For illustrative purposes only, one embodiment of the present invention has a length of about 26½ inches and a height of about 18 inches. The contoured central portion is generally semi-circular and has a length along the bottom wall of the plate of about 12 inches and a maximum height of about 5½ inches.

The above detailed description of this invention has been given for ease of understanding only. No unnecessary limitations should be understood therefrom, as modifications will be obvious to one skilled in the art.

I claim:

1. A restraint device for preventing a person's hands from contacting that person's legs while lying in a bed having side rails, comprising
   a generally flat plate which is positioned in a generally upright manner transversely to the person along the person's waist, said plate having a bottom wall which is contoured to define a base portion at opposite ends which is positioned on said bed on opposite sides of the person's waist, and a central portion which overlies the person's waist, and
   means for releasably securing said plate to said bed.

2. A restraint device as defined in claim 1 wherein the contoured portion of the bottom wall defines a generally semi-circular opening adapted to overlie the waist portion of a person.

3. A restraint device as defined in claim 1 wherein padding is secured to the contoured portion of said bottom wall to soften any contact between the person's waist and said device.

4. A restraint device as defined in claim 1 wherein said securing means comprises a plurality of straps, each strap having one end secured to a marginal side portion of said plate and a free end for securement to the side rails of said bed.

5. A restraint device as defined in claim 1 wherein said device has a length about equal to the width of said bed, and a height about equal to the height of said side rails on said bed.

6. A restraint device for preventing a person's hands from contacting that person's legs while lying in a bed having side rails, comprising
   a relatively flat plate which is positioned in a generally upright manner transversely to the person along the person's waist, said plate having a bottom wall which is contoured to define a base portion at opposite ends which is positioned on said bed on opposite sides of the person's waist, and a central portion which defines a semi-circular opening adapted to overly the person's waist,
   said device having a length about equal to the width of said bed, and a height about equal to the height of said side rails on said bed, and
   padding secured to the contoured portion of said bottom wall to soften any contact between the person's waist and said device, and
   a plurality of straps for securing said plate to said bed, each strap having one end secured to a marginal side portion of said plate, and a free end for securement to the side rails of said bed.

* * * * *